(12) United States Patent
Palmer (10) Patent No.: US 6,579,223 B2
(45) Date of Patent: Jun. 17, 2003

(54) BLOOD PUMP

(76) Inventor: Arthur Palmer, 2236 N. Lincoln Park West, Chicago, IL (US) 60614

( * ) Notice: Subject to any disclaimer, the term of this patent is extended or adjusted under 35 U.S.C. 154(b) by 0 days.

(21) Appl. No.: 09/928,386

(22) Filed: Aug. 13, 2001

(65) Prior Publication Data

US 2003/0032854 A1 Feb. 13, 2003

(51) Int. Cl.$^7$ .................................................. A61F 2/00
(52) U.S. Cl. .......................................... 600/16; 623/3.1
(58) Field of Search .......................... 600/16–18; 623/1, 623/3, 12, 3.1, 3.11, 11.11, 904, 910, 913, 922, FOR 100, FOR 102

(56) References Cited

U.S. PATENT DOCUMENTS

| | | | | |
|---|---|---|---|---|
| 4,133,616 A | * | 1/1979 | Poirier | 417/384 |
| 4,376,312 A | * | 3/1983 | Robinson et al. | 417/388 |
| 4,552,552 A | * | 11/1985 | Polaschegg et al. | 604/6.05 |
| 4,851,002 A | | 7/1989 | Slonina | |
| 4,938,766 A | | 7/1990 | Jarvik | |
| 5,222,980 A | * | 6/1993 | Gealow | 417/474 |
| 6,045,496 A | * | 4/2000 | Pacella et al. | 600/16 |
| 6,464,476 B2 | * | 10/2002 | Ross et al. | 418/55.3 |

FOREIGN PATENT DOCUMENTS

EP 0629412 1/1998

OTHER PUBLICATIONS

Left Ventricular Assist Devices, Management of End–Stage Heart Disease, Chapter 16, pp. 197–211, Argenziano et al., 1998.

Total Artificial Heart, Management of End–Stage Heart Disease, Chapter 17, pp. 213–219, Kung, 1998.

Axial Flow Pumps, Management of End–Stage Heart Disease Chapter 18, pp. 221–227, Fraxier, 1998.

An electromagnetically driven univalved artificial heart, Artificial Heart 3, Chapter 10, pp. 87–91, Nitta et al., 1990.

Development of artificial heart With left and right ventricles using S linear pulse motor, Artificial Heart 3, Chapter 12, pp. 101–105, Umezu et al., 1990.

(List continued on next page.)

*Primary Examiner*—Jeffrey R. Jastrzab
(74) *Attorney, Agent, or Firm*—Greer, Burns & Crain, Ltd.

(57) ABSTRACT

A pump especially designed for pumping blood comprises a bladder, the interior surface area and volume of which is changeable, i.e., it stretches and expands during the filling phase, and elastically contracts to its normal relaxed size during the ejection phase. The bladder has a fluid inlet and a fluid outlet. A device, such as a vacuum pump, alternately expands and contracts the interior surface area and volume of the bladder. Most of the interior surface area of the bladder expands and contracts in each cycle. One or more check valves or other means for causing substantially one-way fluid flow through the bladder are also provided. The pump of the invention decreases the likelihood of blood clots forming in the pump, decreases the risk of damage to blood cells, improves the pumping characteristics of the device, and decreases or eliminates the chance of foreign fluids passing into the blood stream should a tear or break occur in the bladder.

22 Claims, 6 Drawing Sheets

OTHER PUBLICATIONS

Preliminary study—Optimization of spiral vortex blood pump, Artificial Heart 3, Chapter 13, pp. 107–114, Umexu et al., 1990.

Development of an artificial heart actuator for a compliance chamberless blood pump, Artificial Heart 3, Chapter 17, pp. 137–142, Imachi et al., 1990.

Toward a totally implantable artificial heart: Development status at Cleveland Clinic, Artificial Heart 3, Chapter 18, pp. 147–164, Nakamura et al., 1990.

Motor–driven, computer–controlled implantable cardiac assist device—An optical encoer for feedback control, Artificial Heart 3, Chapter 21, pp. 183–197, Nakamura et al., 1990.

The Penn State Implantable artificial heart: Current status, Artificial Heart 3, Chapter 24, pp. 205–212, Snyder et al., 1990.

Design of moving–actuator total, Artificial Heart 3, Chapter 27, pp. 229–233, Goo Min et al., 1990.

Philadelphia Heart System (Cardiac Systems, Japan Medical Supply), Artificial Heart 3, p. 342, Unknown, 1990.

Tohoku University TH–7B pneumatically Driven sac–type ventricular assist device System and newly developed vibrating electromagnetic pump, Artificial Heart 3, p. 345, Unknown, 1990.

* cited by examiner

BLOOD PUMP

FIELD OF THE INVENTION

The present invention relates to pumps and more specifically to blood pumps, ventricular assist devices, and artificial hearts.

BACKGROUND OF THE INVENTION

The natural heart functions in a fashion similar to a positive displacement pump. Each of the two pumping chambers in the natural heart has two check valves (an inlet and an outlet valve). The walls of the natural heart are made of contractile muscle that provide the power to pump the blood. Each pumping cycle consists of a filling or diastolic phase of the pumping cycle and an ejection or systolic phase of the pumping cycle. During the filling phase, the muscle fibers making up the walls of the heart relax allowing the chamber they surround to fill with blood. During the ejection phase of the cycle the muscle making up the walls of the heart contracts ejecting a portion of the blood from the chamber. The check valves assure one-way flow.

Mechanical blood pumps have been developed for use as artificial hearts to replace or assist the natural heart. Present blood pumps which are available to assist or replace the heart fall into two general categories. One category uses a rotary impeller and includes centrifugal pumps and axial flow pumps. The other category is pulsatile pumps, the diaphragm type pump being the most common. Blood pumps may also be classified as internal (intracorporeal) or external (extracorporeal) to the body.

Diaphragm pumps are favored as they provide desirable pulsative flow and are reliable owing to their simplicity. Prior art diaphragm pumps comprise a housing, a flexible but not extensible diaphragm that divides the interior of the housing into two chambers, namely a pumping chamber and a driving chamber. Diaphragms are conventionally fabricated from polyurethane, a flexible but not elastic material. The pumping chamber portion of the housing has an inlet and an outlet, each of which is equipped with a one-way flow check valve. The diaphragm is driven into and out of the pumping chamber mechanically, pneumatically or hydraulically. Mechanical drives typically include a pusher plate on the drive side of the diaphragm connected to a cam, solenoid or other device to impart reciprocal motion to the pusher plate and diaphragm. Alternatively, a drive fluid, either liquid or gas, may be used to reciprocally drive the diaphragm into and out of the pumping chamber.

One of the problems associated with available mechanical blood pumps is the formation of blood clots (thrombosis) in the pump. To address this problem, the interior surfaces of the diaphragm and housing walls that define the pumping chamber are typically designed to have a very smooth surface, in an effort to retard clotting. Other attempts to reduce clotting have involved provision of a rough texture on the interior surfaces of the pumping chamber to encourage endothelial cells, normally lining the heart and blood vessels, to grow over the surfaces eventually providing a smooth surface. Both of these methods work to some degree, but clotting in the device, with clots breaking off and entering the circulatory system, remains a problem.

Another problem relates to the flow of blood through the pump. Significant turbulence occurs in the chamber during the pumping cycle. There is little that can be done to control the characteristics of blood flow through the pumping chamber. There are areas of high velocity and other areas of slow flow. These slow flow areas also contribute to clotting. Turbulence leads to energy loss and inefficiency of the pump. Excessive turbulence may also damage the blood cells.

An additional problem is rupture of the diaphragm. If the diaphragm is driven pneumatically or hydraulically, should a tear or rupture of the diaphragm occur, the driving fluid may be pumped into the bloodstream, causing a harmful and potentially fatal embolism. Even if the pump is mechanically driven, a diaphragm rupture can result in air entering the bloodstream causing an embolism.

The foregoing are long standing problems in the art that have defied solution. There is, therefore, a need in the field for an improved blood pump and ventricular assist device.

OBJECTS OF THE INVENTION

It is an object of the invention to provide a blood pump that reduces the incidence of blood clotting.

It is another object of the invention to provide a blood pump with improved flow characteristics, particularly, to reduce or eliminate stagnant and low velocity flow areas within the pumping chamber to reduce blood clot formation, and to minimize areas of high turbulence to avoid damage to blood cells.

It is also an object of the invention to prevent intrusion of foreign matter into the bloodstream, and especially to prevent embolisms of the driving fluid or other fluids as a result of a pump failure.

SUMMARY OF THE INVENTION

In attainment of these and other objects and advantages of the invention, a pump is provided that has an elastic, extensible or stretchable bladder that expands in the filling phase and contracts in the ejection phase of the pumping cycle. The pump is particularly well suited for pumping blood, as in a ventricular assist device or a total artificial heart. However, the pump of the invention will find applications in other industries and non-medical fields for pumping fluids other than blood. The summary and following detailed description is in reference to, but is not limited to, blood pumping applications.

In a most basic embodiment, the blood pump comprises a bladder, the interior surface area and volume of which is changeable, i.e., it stretches and expands during the filling phase, and elastically contracts to its normal relaxed size during the ejection phase. The bladder has a fluid inlet and a fluid outlet. A device, such as a vacuum pump, compressor, solenoid or cam, alternately expands and contracts the interior surface area and volume of the bladder. A majority of the interior surface area of the bladder expands and contracts a significant amount (more than a few percent) in each cycle. One or more check valves or other means for causing substantially one-way fluid flow through the bladder are also provided.

Looking at the normal heart, there is very little tendency for blood clots to form in the heart when it is working normally. When it is working normally, the muscle which comprises the walls of the heart contracts with each ejection changing the surface area of the lining of the heart. After a patient has sustained a myocardial infarction (heart attack) a portion of the heart muscle comprising the wall of the heart has become necrotic (dead) and a scar has formed in that area. Because that area of the heart is now a scar, rather than muscle, and can no longer contract, it does not change the surface area of the lining of the heart in this localized area.

It has been discovered that in this localized area of the natural heart (the area that does not contract due to a previous heart attack) there is a significant tendency for blood clots to form. This suggests that the change in surface area of the lining of the heart, with each pump cycle, is important in preventing clot formation on the lining of the heart. In a similar fashion, the changing of the surface area of the bladder of the invention as it stretches and contracts with each pumping cycle will decrease or eliminate clot formation on the surface of the bladder.

In a preferred embodiment, the blood pump of the invention comprises a housing, an extensible bladder in the housing, and a void volume or space between the housing and the bladder adapted to be occupied by a driving fluid. The bladder has an inlet and an outlet. At least one check valve is provided at the bladder inlet and/or outlet to provide one-way flow through the bladder. A vacuum source, compressor or other means is provided for altering the pressure of the driving fluid to alternately expand and contract the interior surface area and volume of the bladder. In the preferred embodiment, the driving fluid is a gas, and the driving means alternates pressure between comparatively high and low pressures, the high pressure being at or below atmospheric pressure and the low pressure being significantly below atmospheric. The application of the low pressure causes the bladder to expand and application of the high pressure causes the bladder to contract.

The invention also encompasses a method of pumping. A preferred method comprises the steps of (a) providing an extensible bladder having an inlet and an outlet; (b) connecting the inlet and outlet of the bladder to a person's circulatory system; (c) expanding the interior surface area and volume of the bladder to draw blood into the bladder through the inlet; (d) contracting the interior surface area and volume of the bladder to pump blood out of the outlet of the bladder; and (e) rhythmically repeating steps (c) and (d).

The bladder is preferably made of an elastic material that changes surface area during the pumping cycle. It expands or stretches during the filling phase of the pumping cycle and it returns elastically to its contracted size during the discharge or ejection phase of the pumping cycle. A majority of the interior surface area of the pumping chamber expands and contracts a significant amount (more than a few percent) in each cycle. The change in the area of the bladder surface during the pumping cycle will reduce the incidence and growth of blood clots forming on the surface of the bladder.

In addition, the blood pump of the invention may include variations in the thickness of the bladder and the material comprising the bladder in different areas, segments or portions of the bladder. The thinner areas will stretch more than the thick areas during the filling phase of the pumping cycle. This will draw more blood into the region of the pumping chamber surrounded by the thinner areas of the bladder. Varying the material in different areas of the bladder can also change the amount that various portions of the bladder stretch during the filling portion of the pumping cycle, and in addition, can change the speed at which different areas return to their neutral positions during the ejection part of the pumping cycle. Blood in some areas of the pumping chamber can thus be ejected earlier than blood in other areas. Accordingly, the characteristics of flow into the pumping chamber, through the pumping chamber, and out of the pumping chamber can be controlled and directed. Areas of stagnation can be minimized, further decreasing the likelihood of blood clot formation. Turbulence can also be minimized improving the efficiency of the pump and mitigating damage to blood cells.

In addition to varying the thickness and the material of the bladder, struts of varying elasticity can be molded into the bladder. These struts will bridge from one side to another side of the bladder and aid in maintaining the geometrical shape of the bladder. These struts may also be stretched during the filling portion of the pumping cycle and will provide additional force for ejection during the ejection part of the pumping cycle.

The filling phase of the pumping cycle is advantageously driven pneumatically or by other means for exerting below atmospheric pressure in the space between the housing and the bladder. During the filling phase, blood will be drawn into the pumping chamber and elastic energy will be stored in the bladder. The ejection phase of the cycle will then occur when the negative pressure is released and the bladder returns elastically to its neutral position. Although some positive pressure may be used on the bladder during the ejection phase of the pumping cycle, preferably and ideally there will be no positive pressure exerted on the bladder and all the force for ejection will come from the elastic recoil of the bladder. In this situation, when the power for ejection comes entirely from the elasticity of the bladder and no positive fluid pressure is exerted on the bladder, should a break or tear occur in the bladder, there is very little chance that any significant amount of the driving fluid would enter the circulatory system as there is no positive pressure to drive it through the tear or break in the bladder.

For the foregoing reasons, the blood pump of the invention decreases the likelihood of blood clots forming, improves the pumping characteristics of the device, and decreases or eliminates the chance of foreign fluids passing into the blood stream should a tear or break occur in the bladder. Although the pump of the invention was initially conceived for pumping blood, it also will find utility for pumping fluids in industrial and non-medical fields. Other attributes and benefits of the present invention will become apparent from the following detailed specification when read in conjunction with the accompanying drawings.

DETAILED DESCRIPTION OF THE PREFERRED EMBODIMENT

The following is a detailed description of certain embodiments of the invention presently deemed by the inventor to be the best mode of carrying out his invention. The invention as defined by the appended claims is not limited to these embodiments, and additional embodiments of the claimed inventive concept will undoubtedly be apparent to those skilled in the art.

Referring to the drawings, FIGS. 1A–1G show a first embodiment of the pump of the invention, comprising a pump 10 of linear configuration. The linear configuration is simple and demonstrates the concept in an easily understood fashion. Pump 10 comprises an elastic bladder 12 within a shell or housing 14. The bladder in this embodiment is substantially cylindrical and the shell is football shaped, and of a diameter larger than that of the bladder. The elastic bladder comprises a large portion of the surface area of the pumping chamber. The bladder is sealingly connected to the shell or housing at both of its ends. The bladder has an inlet 16 and an outlet 18. An inlet check valve 20 and an outlet check valve 22 insure one-way flow through the bladder. A void volume, space or chamber 24, in this embodiment, an annular space or chamber 24, is defined between the bladder 12 and housing 14. A bladder actuating or driving fluid is adapted to be cyclically introduced into and removed from the annular space 24 through port 26. Various means known in the art are commercially available for introducing actuating fluid into and removing actuating fluid from the space 24.

The bladder may be constructed of any elastic or extensible material, such as a natural or artificial latex. It is important that the bladder be fabricated of biocompatible material, that is durable and capable of withstanding numerous expansion-contraction cycles.

It is further contemplated that the bladder could be formed of a semisolid material, and that the driving fluid could be the same semisolid material, the driving material and bladder being a unitary body or mass. Thereby the adding or withdrawing of semisolid material from the housing would cause the surface area and volume of the pumping chamber to expand and contract.

Figure 1A:
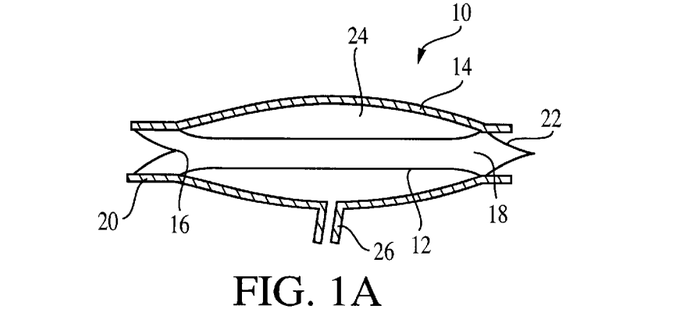
FIGS. 1A though 1G schematically depict a first embodiment of the pump of the invention, and illustrate the pumping cycle of the same.

The housing 14 is fabricated of a rigid material such as titanium or a semi-rigid material such as an elastomer.

The check valves 20 and 22 may be natural, such as pig valves, or artificial, both of which are commercially available.

The driving fluid may be a gas, liquid or gel. Preferably, it is a gas, such as carbon dioxide. Carbon dioxide is desirable as it can be rapidly absorbed in blood in the event of a bladder tear or rupture. Although the bladder may be driven with positive pressure, it is preferred that operating pressures be at or below atmospheric. More specifically, the fluid is driven cyclically between a high pressure that is approximately atmospheric and a low pressure substantially below atmospheric. The requisite differential in pressure depends on various factors, including the resiliency of the bladder and the volume change within the bladder that is desired in each pumping cycle.

FIGS. 1A–1G illustrate the pumping cycle. FIG. 1-A shows the bladder 12 at the end of the ejection or discharge phase; i.e., in a contracted neutral condition. If, as is preferred, a negative pressure source is used to drive the bladder, space 24 would at this time be at or near atmospheric pressure and the bladder would be in its relaxed state. At this stage of the pumping cycle, the interior surface area of the bladder 12 is at a minimum. Both the inlet check valve 20 and the outlet check valve 22 are closed.

Figure 1B:
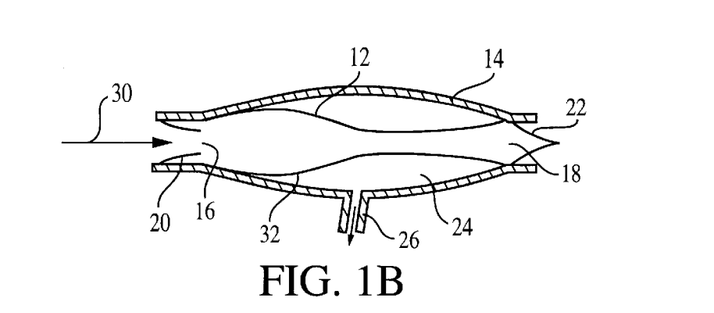

FIG. 1B illustrates an early stage in the filling phase. Driving fluid is being evacuated or extracted from the space 24, reducing the pressure therein to sub-atmospheric and causing the bladder to expand. As the bladder expands, it generates a low pressure within the bladder, causing the inlet valve to open and blood to enter the bladder in the direction indicated by the arrow 30. Preferably, a portion 32 of the bladder 12 adjacent to inlet 16 is expanded initially.

Figure 1C:
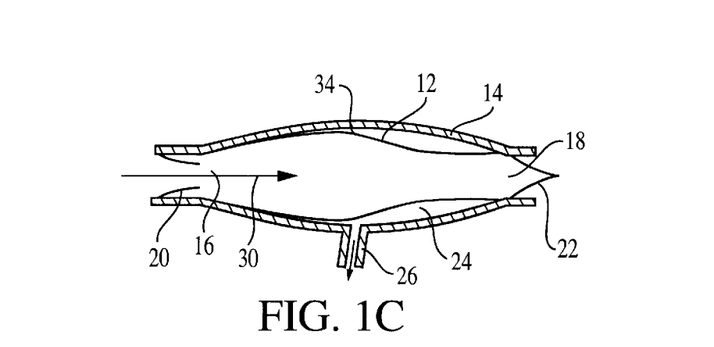

FIG. 1C illustrates a mid-portion of the filling phase. As driving fluid continues to be extracted from space 24, the bladder continues to expand and draws more blood into the bladder. Compared to FIG. 1B, the bladder is shown as having progressively expanded in the direction of the outlet 18.

Figure 1D:
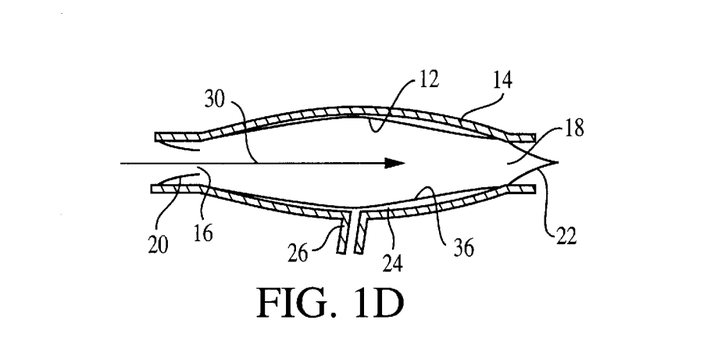

FIG. 1D illustrates a late stage of filling. Space 24 has been substantially completely evacuated and the bladder has been substantially completely expanded. The interior surface area 36 and the volume of the bladder 12 are now at a maximum. Arrow 30 shows the extent of inflow of blood into the bladder.

Figure 1E:
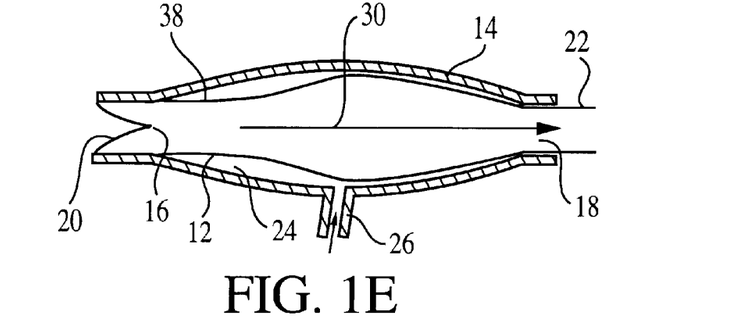

FIG. 1E shows an early stage in the ejection or discharge phase of pump operation. Driving fluid is being re-introduced at a controlled rate into the space 24, causing the bladder to commence contracting, which in turn causes the inlet check valve to close, the outlet check valve to open and blood to commence flowing through the outlet, as shown by the arrow. Portion 32 of the bladder is illustrated as being initially contracted.

Figure 1F:
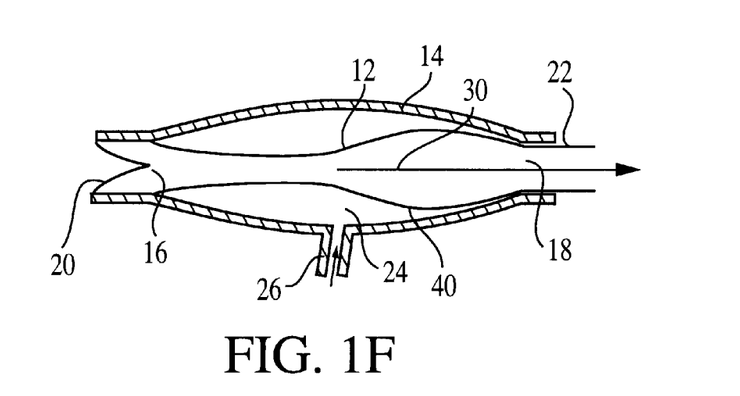

FIG. 1F shows a mid-portion of the ejection or discharge phase. As driving or actuating fluid has continued to enter the space 24, contraction has progressed in the direction of the outlet to a mid-portion 40 of the bladder. Arrow 30 illustrates continuous ejection of blood through the outlet 18.

Figure 1G:
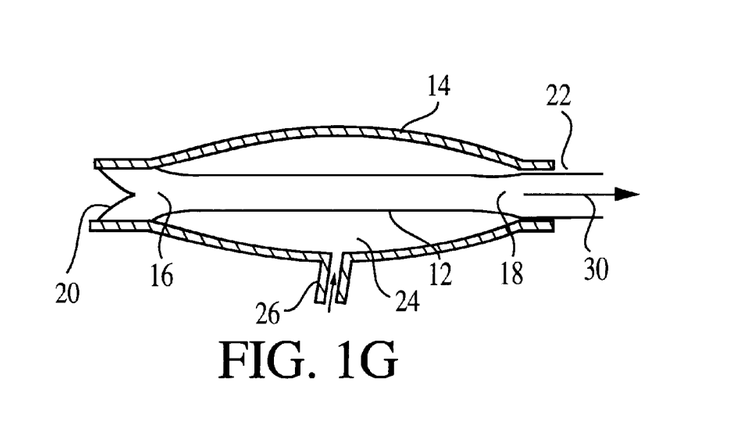

FIG. 1G shows a late stage of the ejection or discharge phase. Due to substantially complete filling of the space 24 with actuating fluid, the bladder has been restored to very nearly the original contracted state shown in FIG. 1A. At this stage, approximately the same volume of blood as had been drawn in during the filling stage has been expelled from the pumping chamber through the outlet. It is not necessary, nor desirable in many applications, to expel all of the blood from the pumping chamber.

Upon completion of the discharge or ejection phase, the bladder is fully contracted, the check valves are closed, and the pump is prepared to repeat its cycle of operation at such pulse rate as may be dictated by the attending physician.

Throughout the pumping cycle, the interior surface area of the bladder changes. Different portions of the interior surface of the bladder may change to a smaller or greater degree. For example, the portions of the bladder adjacent to the inlet and outlet may expand/contract to a smaller degree than the central portion of the bladder as shown in FIGS. 1A–G. It is preferable, to prevent or reduce blood clot formation, that the surface area of most of the bladder expand/contract at least a few percent.

Furthermore, it is desirable that a majority of the overall interior surface area of the pump (i.e., the bladder, inlet, outlet and valves) comprise elastic or stretchable material that will change, i.e., expand and contract during the pumping cycle. It may be necessary or desirable, however, in some applications, to form valves or other components of inextensible material. For blood pump applications, it is desirable to maximize the interior surface area of the pump that will expand/contract. In accordance with the present invention, a majority of the interior surface area of the bladder and pump will expand/contract at least a few percent during the pumping cycle. Consequently, the likelihood of blood clot formation will be substantially reduced.

Due to the smooth internal configuration or shape of the bladder 12 and the manner in which blood is "milked" into and through the bladder, as depicted in FIGS. 1A–1G, there are no areas within the path of blood flow that can become stagnant, diminishing the potential for damage to blood cells caused by undue turbulence and also diminishing clot formation.

A second embodiment of the invention is illustrated in FIGS. 2A–2G as residing in a curved configuration that is somewhat more representative of the shape of a natural heart. The curved configuration may prove to be a better choice for surgical implantation. Parts and features of the blood pump of FIGS. 2A–2G that are the same as or similar to the parts and features of the embodiment of FIGS. 1A–1G are indicated by the same reference numerals but using numerals in the 100 series. The letter suffixes in the FIG. 2 series of illustrations correspond to the like suffixes in FIG. 1 in terms of illustrating the pumping cycle.

Figure 2A:
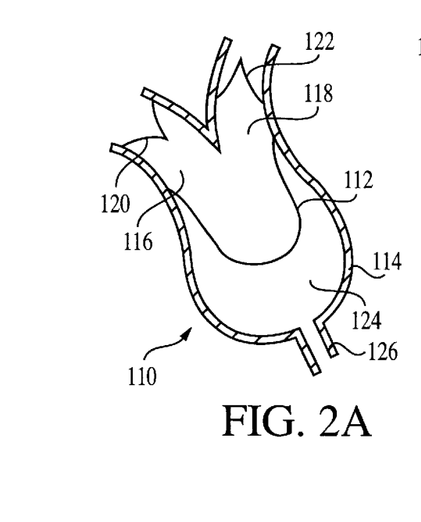
FIGS. 2A through 2G show schematically a second embodiment of the invention, again illustrating the pumping cycle of the pump of the invention.

The pump 110 comprises a cup or bag shaped bladder 112, comprised of an expandable and contractible elastic material. At its upper end, the bladder is bifurcated to form an inlet conduit 116 containing an inlet check valve 120 and an outlet conduit 118 containing an outlet check valve 122. Inlet 116 corresponds more or less to the vena cava of the human heart and outlet 118 corresponds more or less to the aorta of the human heart.

The bladder is encased in and sealed to the open end of a cup or sack shaped housing or shell 114 that is complementary to but of larger size than the bladder 12 and that defines a void volume, chamber or space 124 between the shell and the bladder. A conduit 126 establishes fluid communication between the space 124 and a means, such as a vacuum pump system hereinafter described, for cyclically evacuating and filling the chamber 124 with a bladder actuating or driving fluid.

Figure 2B:
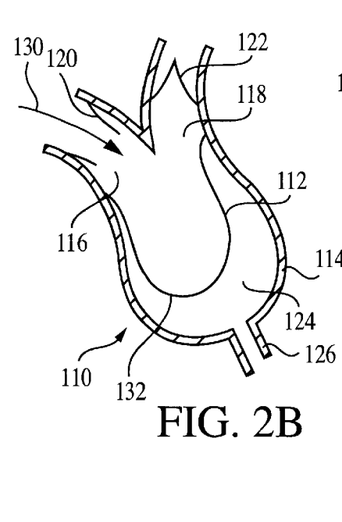
Figure 2C:
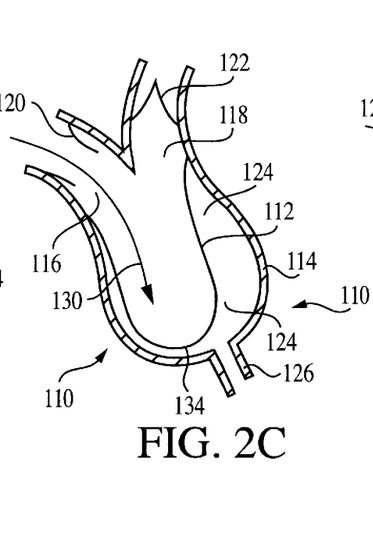
Figure 2D:
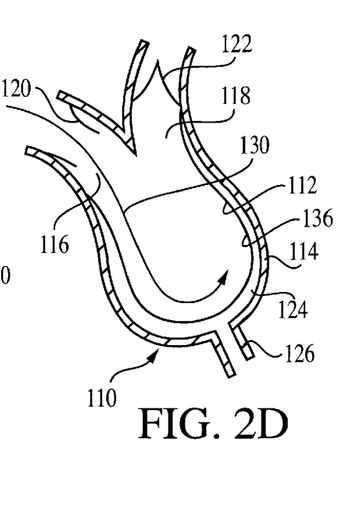
Figure 2E:
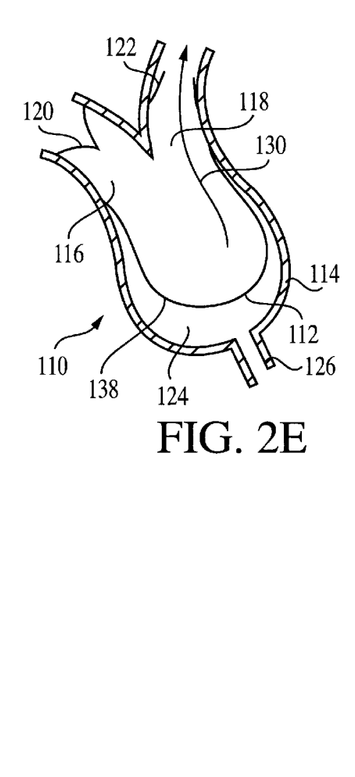
Figure 2F:
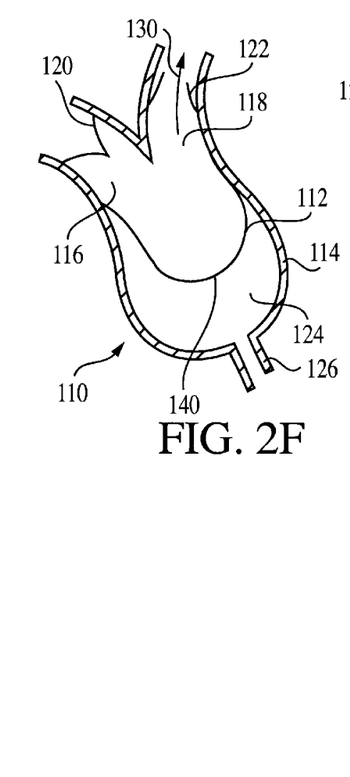
Figure 2G:
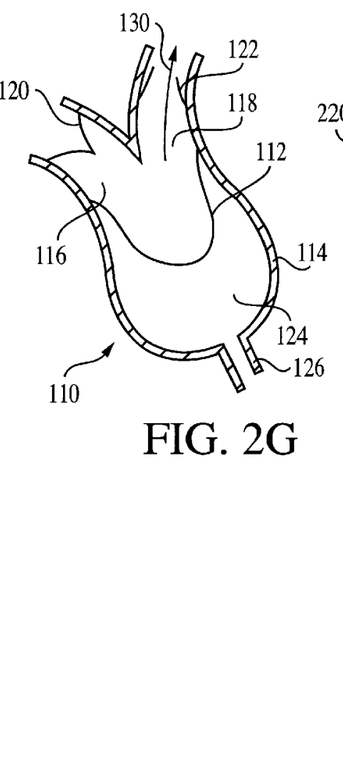

In the neutral position shown in FIG. 2A, the bag or bladder 112 is fully contracted, the inlet and outlet valves 120 and 122 are closed, and the chamber 124 is filled with actuating fluid. As actuating fluid is withdrawn at a controlled rate from chamber 124, the bladder 112 is progressively expanded to cause the inlet valve to open and to cause blood to be gradually drawn into the bladder from the inlet 116, as depicted in FIGS. 2B–2C, until the bladder is fully expanded and filled with blood, as depicted in FIG. 2D. Evacuation of the chamber 124 is then stopped, and actuating fluid gradually bled back into the chamber 124, to cause the bladder to contract and expel or discharge blood through the outlet 118, as illustrated in FIGS. 2E–2G, until the volume of blood taken in during the fill phase has been expelled and the bladder returned to the neutral retracted position shown in FIG. 2A, whereupon the pumping cycle may be cyclically repeated at a pulse rate established by the attending physician.

As with the embodiment of FIGS. 1A–1G, the embodiment of FIGS. 2A–2G does not have any obstructions likely to cause turbulent flow and does not have any stagnant areas. Consequently, damage to blood cells and/or clotting and/or clot growth are mitigated.

Figure 3:
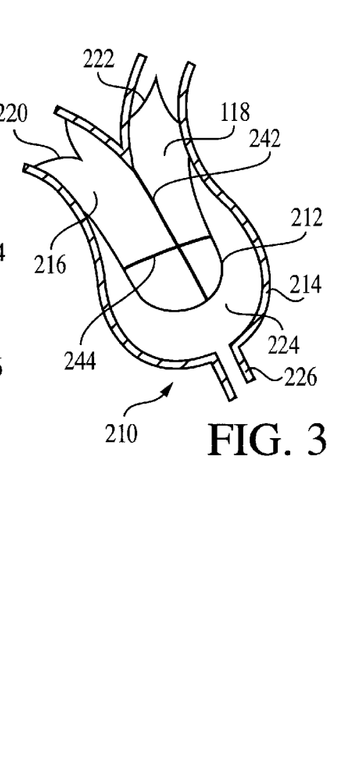
FIG. 3 shows a third embodiment of the invention incorporating struts.

FIG. 3 illustrates a third embodiment of the pump of the invention. As in the first two embodiments like numerals represent like parts, but with numerals in the 200 Series. The third embodiment, indicated at 210, is characterized by struts 242,244 bridging the interior of bladder 212. The struts are constructed internally from one wall of the bladder to another. These will help maintain the geometric shape of the pumping chamber as the bladder is stretched. The struts may also be made of an elastic material. They will then stretch during the filling phase of the pumping cycle and elastically recoil in the ejection phase to add to the pumping force.

Figure 4:
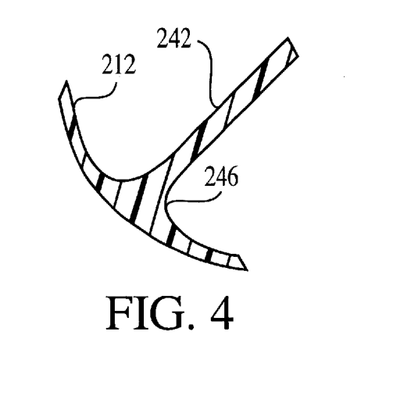
FIG. 4 shows a detail of a strut—bladder connection.

FIG. 4 illustrates one preferred manner of attachment of a strut 242 to the bladder wall 212. Preferably the strut and bladder are integrally formed with the strut having a flared end 246. The flared end functions to spread the load carried by the strut over a greater area to improve function and durability. Alternatively, other means known to those skilled in the art may be used to accomplish the same result.

Figure 5:
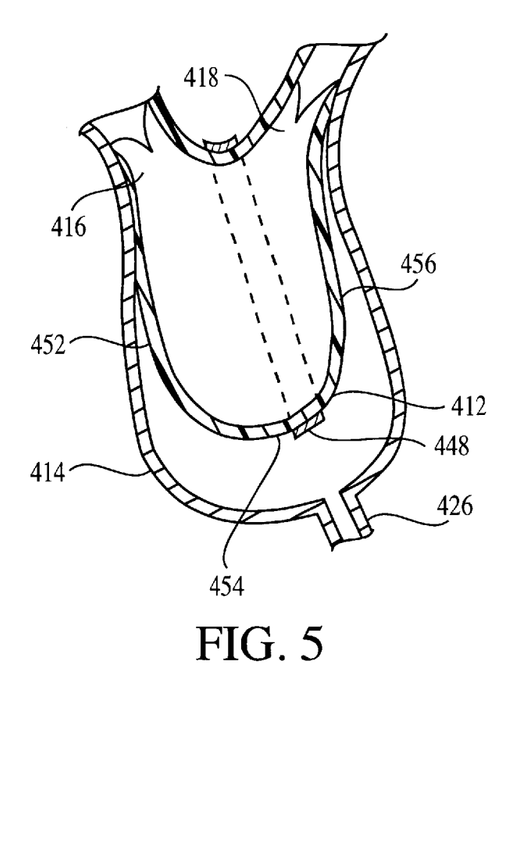
FIG. 5 shows a fourth embodiment of the invention having a bladder of varying thickness, and having bands.

FIG. 5 illustrates a fourth embodiment of the invention similar to the second embodiment but with bands and a bladder of varying wall thickness. Parts and features of the blood pump of FIG. 5 that are the same as or similar to the parts and features of the embodiment of FIGS. 2A–2G are indicated by the same reference numerals but using numerals in the 400 series. The fourth embodiment includes optional elastic band 448 on the exterior of bladder 412. One or more such bands may be used to maintain the dimensional stability of the bladder in the same manner as the struts described in the previous embodiment. Further, bladder 412 is tapered in wall thickness. The bladder wall 452 is thinner adjacent inlet 416, becomes somewhat thicker at midpoints 452 and 454, and is thickest at 456, adjacent the outlet 418. By varying the thickness of the bladder in different areas, thin areas 452 of the bladder will stretch earlier to a greater degree than other areas during the filling phase of the pumping cycle. Some areas of the bladder such as thicker areas 456 will return to their neutral position more quickly than others during the ejection or discharge phase. By this means, the flow of blood can be directed, in a predetermined manner, through the pumping chamber. Areas of stagnation can be minimized or eliminated to decrease the potential for clotting, and areas of turbulence can be avoided to increase the efficiency of the pump and decrease damage to blood cells. Alternative variations will be readily apparent to those skilled in the art whereby the bladder may be designed to be thicker in some areas and thinner in others. The material composition of the bladder may also be varied to achieve similar results.

Figure 6:
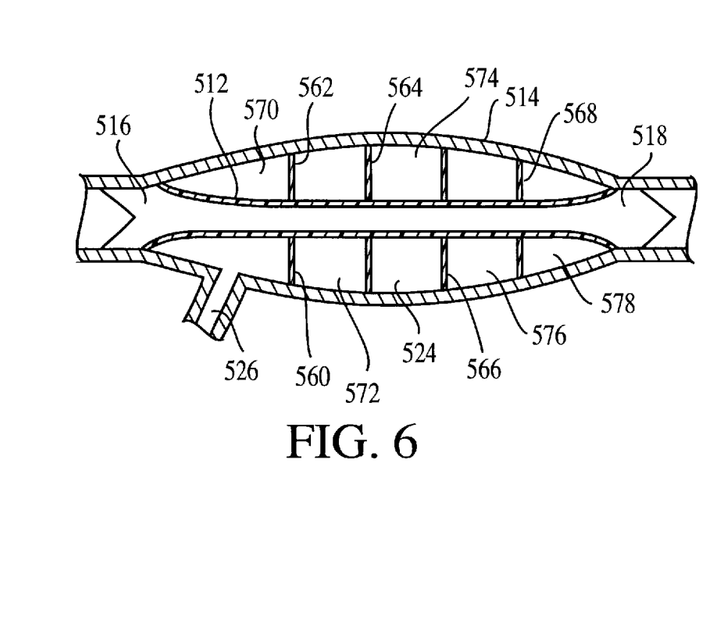
FIG. 6 shows a fifth embodiment of the invention with means for regulating the flow of driving fluid into and out of the void volume or space between the housing and bladder.

Another means for controlling the expansion and contraction rates of the bladder is shown in a fifth embodiment in FIG. 6. Again, like numerals refer to like parts, but in the 500 sequence. A driving fluid flow regulating means 560 is provided in the space 524 between the housing and bladder. One or more annular walls 562, 564, 566, 568 are provided between the housing and bladder, thereby compartmentalizing the annular space 24. Each wall may have one or more holes (not shown) to connect adjoining compartments. The number and sizes of the holes will regulate the flow rate between compartments, so that the pressure in each compartment at any given time may be controlled. On the initial application of a vacuum or low pressure through port 526, the pressure in space 570 will drop rapidly, while the pressure in the remaining compartments will drop at slower rates. As a result, the portion of the bladder adjacent compartment 570 will expand initially to a greater degree than the bladder portions adjacent other compartments. As the low pressure through port 526 is maintain, the pressure in each adjacent chamber 572–578 will equalize over a period of time, dependent on the number an size of the holes in the walls 562,564,566,568 separating compartments. This in turn will cause the bladder to expand in a sequence similar to that shown in FIGS. 1A–1D.

Alternative means are likely known to those skilled in the art for regulating fluid flow and fluid pressure in the space between the bladder and housing. For example, each compartment 570,572,574,576,578 could be sealed from the other compartments, and the pressure in each compartment could be independently regulated by plural fluid pressure control tubes connected to each compartment, respectively.

Figure 7:
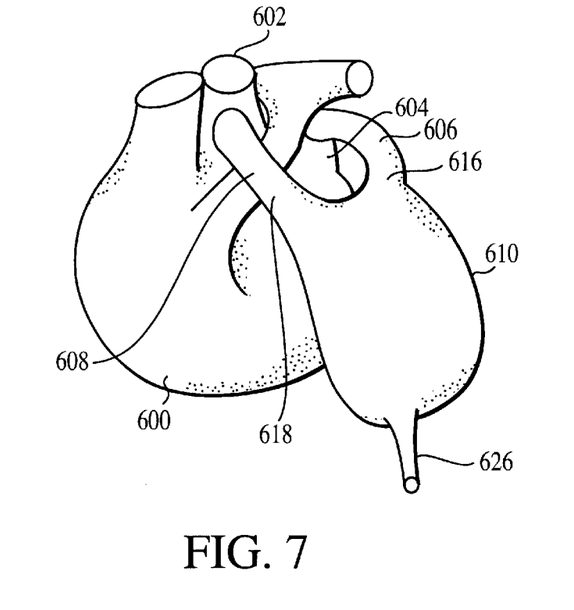
FIG. 7 illustrates the blood pump of the invention connected to a human heart as a left ventricular assist device.

FIG. 7 shows a blood pump 610 of the invention applied as a left ventricular assist device. A tube or other conduit 606 connects the left atrium 604 to the inlet 616 of the pump. Similarly, a second tube 608 connects the pump outlet 618 to the aorta 602.

Figure 8:
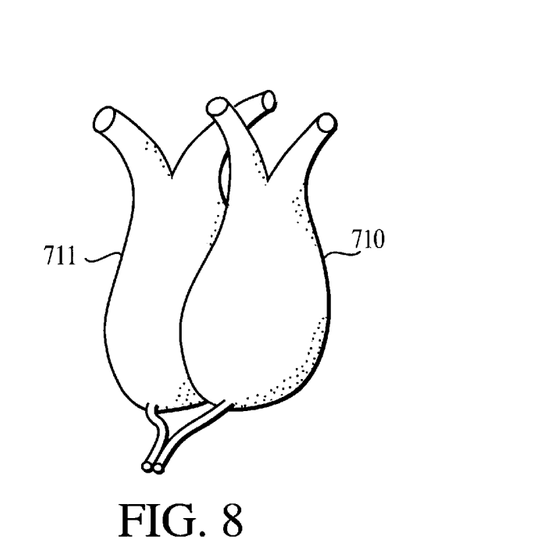
FIG. 8 illustrates a combination of two pumps connected to form a total artificial heart.

FIG. 8 depicts a total artificial heart comprising two pumps 710 and 711 of the invention.

Figure 9:
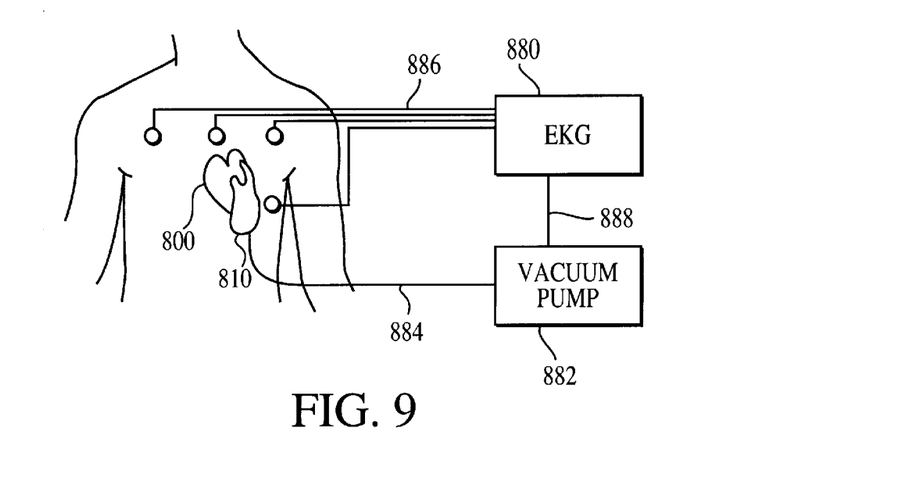
FIG. 9 diagrammatically illustrates an internal blood pump driven with an external pneumatic system.

FIG. 9 schematically shows a representative system for an externally driven left ventricular assist device including a blood pump 810 connected to a heart 800, i.e., as discussed in reference to FIG. 7. The cyclical evacuation and filling of the space or chamber 824 of the pump may, for example, be accomplished using a closed circuit carbon dioxide filled vacuum pump system 882 connected to pump 810 through tube 884. Vacuum pump 882 includes a reservoir for receiving carbon dioxide evacuated by the vacuum pump from the blood pump actuating fluid chamber during the intake or filling phase, and for bleeding carbon dioxide at a controlled rate back into the actuating fluid chamber during the discharge or ejection phase of the pump cycle. The rate of fluid evacuation and the rate of fluid return are each readily controllable. A suitable control means is an electro cardiogram 880 that is operatively linked to the patient and the vacuum pump 882 through cables 886 and 888, as is well known in the art. Alternatively, devices other than EKG 880 may be used for controlling the pumping cycle.

While preferred embodiments of the present invention have been shown and described, it is to be understood that these represent the best mode of practicing the invention contemplated by the inventors at the present time, and that various modifications and changes could be made thereto without departing from the scope of the invention as defined in the appended claim

What is claimed is:

1. A fluid pump comprising:
    an elastic bladder, at least a portion of the interior surface area of said bladder being changeable between a contracted state have a first surface area and an expanded state having a second surface area that is substantially greater than said first surface area, said bladder having a fluid inlet and a fluid outlet;
    means for causing substantially one-way fluid flow through said bladder;
    a housing around at least a portion of said bladder, an annular volume being defined in the space between said housing and said bladder, said annular volume being occupied by a driving fluid;
    means for changing the pressure of said driving fluid in said annular volume to alternately expand and contract said bladder to change the interior surface area and volume of said bladder; and
    a fluid flow regulating means in said annular volume between said bladder and said housing for expanding and contracting selected areas of said bladder adapted, in a filling phase, to expand a selected area of said bladder adjacent said inlet and thereafter progressively expand the remaining areas of said bladder towards said bladder outlet, and during an ejection phase, to initially contract said bladder adjacent said bladder inlet and thereafter progressively contract the remaining areas of the bladder towards said bladder outlet.

2. A fluid pump as in claim 1, wherein said actuating fluid is a gas and said pressure changing means comprises a vacuum pump.

3. A fluid pump as in claim 1, wherein said actuating fluid is a liquid and said pressure changing means comprises a hydraulic pump.

4. A fluid pump as in claim 1, wherein said actuating fluid is a gel.

5. A fluid pump as in claim 1, wherein said means for causing substantially one-way fluid flow comprises at least one check valve.

6. A fluid pump as in claim 1, further comprising means for controlling the expansion and contraction of said bladder.

7. A blood pump as in claim 6, further comprising at least one extensible strut spanning the interior of said bladder.

8. A fluid pump as in claim 1 for use as a ventricular assist device for a heart, wherein said outlet from said bladder is configured for connection to the aorta of the heart.

9. A fluid pump as in claim 1 for pumping blood and comprising two said bladders working in combination to simulate the left and right ventricles of a heart.

10. A fluid pump comprising, an elastic bladder, at least a portion of the interior surface area of said bladder being changeable between a contracted state having a first surface area and an expanded state having a second surface area that is substantially greater than said first surface area, said bladder having a fluid inlet and a fluid outlet;
    a housing around at least a portion of said bladder and defining a space between said housing and said bladder for receiving a bladder actuating fluid;
    means for alternately increasing and decreasing the pressure of said actuating fluid for alternately expanding and contracting said bladder to change the interior surface area and volume of said bladder;
    means for causing substantially one-way fluid flow through said bladder; and
    wherein said bladder and said actuating fluid are a unitary body of semisolid material, the surface of said semisolid material functioning as said bladder interior surface.

11. A method of pumping blood in the circulatory system of a human in the need thereof comprising the steps of
    (a) providing a blood pumping system having an extensible and contractible bladder, said pumping system having an inlet and an outlet;
    (b) connecting the inlet and outlet of said pumping system to the human's circulatory system;
    (c) expanding a majority of the interior surface area of said pumping system by at least a few percent, including expanding the volume of the bladder to draw blood into the bladder through the inlet;
    (d) contracting a majority of the interior surface area of said blood pumping system by at least a few percent, including contracting the volume of the bladder to pump blood out of the outlet of said system; and
    (e) rhythmically repeating steps (c) and (d).

12. A fluid pump comprising:
    a bladder, at least a portion of the interior surface area of said bladder being changeable, said bladder having a fluid inlet and a fluid outlet, said bladder having thickness variations for controlling the expansion and contraction of said bladder, said bladder have a thinner wall thickness at said inlet and a thicker wall thickness at said outlet;

means for alternately expanding and contracting said bladder to change the interior surface area and volume of said bladder; and means for causing substantially one-way fluid flow through said bladder.

13. A fluid pump comprising:

a bladder, at least a portion of the interior surface area of said bladder being changeable, said bladder having a fluid inlet and a fluid outlet;

means for alternately expanding and contracting said bladder to change the interior surface area and volume of said bladder;

means for causing substantially one-way fluid flow through said bladder; and at least one extensible strut spanning the interior of said bladder for controlling its expansion and contraction.

14. A fluid pump comprising:

a bladder, at least a portion of the interior surface area of said bladder being changeable, said bladder having a fluid inlet and a fluid outlet;

means for alternately expanding and contracting said bladder to change the interior surface area and volume of said bladder;

means for causing substantially one-way fluid flow through said bladder; and one or more bands on said bladder for controlling its expansion and contraction.

15. A fluid pump comprising:

a housing;

an extensible and contractible bladder in said housing, a space defined between said housing and said bladder for receiving a bladder driving fluid, said bladder having an inlet and an outlet;

a check valve to at least one of said bladder inlet and outlet;

means for altering the pressure of the driving fluid to alternately expand and contract the interior surface area and volume of said bladder to define a pumping cycle, most of said interior surface area of said bladder adapted to expand and contract with each said pumping cycle; and a fluid pressure regulator in said space to selectively control the rate of expansion or contraction of selected areas of said bladder.

16. A fluid pump as in claim 15 for pumping blood, wherein said bladder is has a curved configuration representative of a natural heart with said inlet being adjacent said outlet.

17. A method for reducing the formation of blood clots during blood pumping, the method comprising the steps of:

providing a blood pump having an elastic bladder having an interior and an interior surface area; and changing said interior surface area by alternately elastically stretching said bladder and elastically contracting said bladder, said changing surface area operative to reduce the formation of blood clots on said interior surface area.

18. A method for reducing the formation of blood clots during blood pumping as defined by claim 17, wherein said elastic bladder is enclosed in a housing, a space defined between said bladder and said housing, and wherein the step of stretching and contracting said bladder includes elastically stretching said bladder by decreasing pressure in said space to below atmospheric, and contracting said bladder by increasing the pressure in said space.

19. A method of for reducing the formation of blood clots during blood pumping as in claim 17, wherein step of changing the interior surface area of said bladder includes changing a majority of the interior surface area of said pump.

20. A method of for reducing the formation of blood clots during blood pumping as in claim 17, wherein said stretching step is a filling phase comprising expanding a selected area of said bladder adjacent said inlet and thereafter progressively expanding the remaining areas of said bladder towards said bladder outlet; and said contracting step is an ejection phase, comprising initially contracting said bladder adjacent said inlet and thereafter progressively contracting the remaining areas of said bladder towards said outlet.

21. A method of for reducing the formation of blood clots during blood pumping as in claim 17, wherein said bladder is has a curved configuration representative of a natural heart with said inlet being adjacent said outlet, and wherein said steps of elastically expanding and contracting said bladder comprises milking the blood through said bladder in a smooth flow substantially free from areas of turbulence and areas of stagnation.

22. A fluid pump comprising:

a bladder, at least a portion of the interior surface area of said bladder being changeable, said bladder having a fluid inlet and a fluid outlet;

means for alternately expanding and contracting the bladder to change the interior surface area and volume of said bladder;

means for causing substantially one-way fluid flow through said bladder; and wherein said bladder is comprised of a plurality of different materials to control the rate of expansion or contraction of selected areas of said bladder.

* * * * *